US008976236B2

(12) United States Patent
DeLand (10) Patent No.: US 8,976,236 B2
(45) Date of Patent: Mar. 10, 2015

(54) SURGICAL LIGHT AND VIDEO CONTROL SYSTEM AND METHOD OF USE

(76) Inventor: Mary Maitland DeLand, Lafayette, LA (US)

( * ) Notice: Subject to any disclaimer, the term of this patent is extended or adjusted under 35 U.S.C. 154(b) by 577 days.

(21) Appl. No.: 13/291,552

(22) Filed: Nov. 8, 2011

(65) Prior Publication Data

US 2013/0113909 A1    May 9, 2013

(51) Int. Cl.
*H04N 7/18* (2006.01)
*A61B 19/00* (2006.01)

(52) U.S. Cl.
CPC ............ *A61B 19/5202* (2013.01); *H04N 7/181* (2013.01); *A61B 19/5212* (2013.01); *A61B 2019/5248* (2013.01)
USPC ................................. 348/77; 348/31; 348/135

(58) Field of Classification Search
CPC ............................ F21W 2131/205; H04N 7/18
USPC ..................................... 348/131, 77, 135–139
See application file for complete search history.

(56) References Cited

U.S. PATENT DOCUMENTS

| 3,360,640 | A | | 12/1967 | Seitz et al. | |
|---|---|---|---|---|---|
| 3,891,842 | A | * | 6/1975 | Strusinski | 396/200 |
| 4,639,838 | A | * | 1/1987 | Kato et al. | 362/33 |
| D336,146 | S | | 6/1993 | Yamada et al. | |
| 5,745,545 | A | * | 4/1998 | Hughes | 378/65 |
| 5,803,905 | A | * | 9/1998 | Allred et al. | 600/249 |
| 5,808,680 | A | * | 9/1998 | Steckhan | 348/370 |
| 5,825,413 | A | * | 10/1998 | Mullis | 348/155 |
| 5,835,266 | A | * | 11/1998 | Kitajima | 359/384 |
| 6,160,582 | A | * | 12/2000 | Hill | 348/370 |
| 6,290,645 | B1 | * | 9/2001 | Goldfarb et al. | 600/249 |
| 6,434,329 | B1 | * | 8/2002 | Dube et al. | 396/14 |
| 6,633,328 | B1 | * | 10/2003 | Byrd et al. | 348/143 |
| 6,817,585 | B2 | * | 11/2004 | Wagner et al. | 248/324 |

(Continued)

FOREIGN PATENT DOCUMENTS

| DE | 102008027909 | 4/2010 |
|---|---|---|
| DE | 102008057820 | 5/2010 |
| DE | 102009051994 | 5/2011 |
| EP | 0421130 | 4/1991 |

OTHER PUBLICATIONS

ADMECO-Lux surgical light with color video system, Medical Engineering, 2001, 2 pages.

(Continued)

*Primary Examiner* — Christopher S Kelley
*Assistant Examiner* — Deirdre Beasley
(74) *Attorney, Agent, or Firm* — Eric L. Sophir; Dentons US LLP (57) ABSTRACT

A system for illuminating and recording an image of an operative field during a medical procedure is presented. The system includes a first light source assembly, a second light source assembly, and a controller. The first and second light source assemblies include a light source operable to illuminate the operative field, a camera operable to record the image of the operative field, and a sensor operable to detect motion from the light source assemblies. The controller is in communication with the first and second light source assemblies. The controller is configured to send operational commands to the light source assemblies based on feedback from the sensors. One of the operational commands is a recording command. The controller is configured to send the recording command to either the camera in the first or second light source assembly.

20 Claims, 3 Drawing Sheets

(56) References Cited

U.S. PATENT DOCUMENTS

| | | | |
|---|---|---|---|
| 6,909,465 B2* | 6/2005 | Liang | 348/373 |
| 7,098,956 B2* | 8/2006 | Keitel et al. | 348/370 |
| 7,224,472 B2 | 5/2007 | Bauch et al. | |
| 7,321,385 B2* | 1/2008 | Rus et al. | 348/69 |
| 7,443,417 B1* | 10/2008 | Heinrich | 348/66 |
| 7,567,833 B2* | 7/2009 | Moctezuma De La Barrera et al. | 600/424 |
| 7,702,379 B2* | 4/2010 | Avinash et al. | 600/424 |
| 8,038,614 B2* | 10/2011 | Gobeyn et al. | 600/300 |
| 8,295,909 B2* | 10/2012 | Goldbach | 600/424 |
| 8,372,003 B2* | 2/2013 | St. George et al. | 600/178 |
| 8,519,984 B2* | 8/2013 | Elsasser et al. | 345/179 |
| 8,565,860 B2* | 10/2013 | Kimchy et al. | 600/436 |
| 2002/0015296 A1* | 2/2002 | Howell et al. | 362/11 |
| 2002/0113890 A1 | 8/2002 | Liang | |
| 2003/0021107 A1* | 1/2003 | Howell et al. | 362/147 |
| 2003/0142204 A1* | 7/2003 | Rus et al. | 348/65 |
| 2003/0164953 A1* | 9/2003 | Bauch et al. | 356/611 |
| 2005/0008204 A1* | 1/2005 | Xu | 382/128 |
| 2006/0104071 A1 | 5/2006 | Parsons | |
| 2006/0119701 A1 | 6/2006 | King | |
| 2007/0014567 A1* | 1/2007 | Rossner et al. | 396/429 |
| 2008/0285820 A1* | 11/2008 | Voelker | 382/128 |
| 2009/0024023 A1* | 1/2009 | Welches et al. | 600/424 |
| 2009/0086495 A1* | 4/2009 | Chen | 362/427 |
| 2011/0037840 A1 | 2/2011 | Hiltl et al. | |
| 2013/0086674 A1* | 4/2013 | Horvitz et al. | 726/19 |
| 2013/0088359 A1* | 4/2013 | Monaci et al. | 340/691.8 |

OTHER PUBLICATIONS

Akridge, Surgical lights, tables and workstations: OR staples steal the show, Healthcare Purchasing news, 1994, Downloaded from internet at http://findarticles.com/p/articles/mi_m0BPC/is_5_28/ai_n6365027/?tag=content;col1, 12 pages.

DE 102008027909 published Apr. 15, 2010, English abstract, downloaded from espacenet.com, 1 page.

DE 102008057820 published May 20, 2010, English abstract, downloaded from espacenet.com, 1 page.

DE 102009051994 published May 12, 2011, English abstract, downloaded from espacenet.com, 1 page.

EP 0421130 published 0 Apr. 1991, English abstract, downloaded from espacenet.com, 1 page.

Graschew, Design and Implementation of Satellite-Based Networks and Services for Ubiquitous Access to Healthcare, InTech, 2010, pp. 115-132.

www.mavig.eu/124-1-m3f--m3df-video-function.html, Integrated OR video system (optional), MAVIG, 1 page.

Merivaara range of surgical lights, Meriled for surgical procedures, 2009, 8 pages.

New outlooks for remote consultations in pathomorphology, Coolscope+DiViSy, 2005, pp. 3-10.

www.amico.com/acc/pdf/clinical/LED_Lights_Brochure.pdf, Pearl Series, Clinical Amico, 2010, 2 pages.

Smith, SELECTPlus Quotation Analysis, Plymouth Health System Executive Summary, pp. 1-22.

The LED Revolution, Dr. Mach Medical Lighting and Technology, 2009, 10 pages.

United States Court of International Trade Proceedings, *Trumpf Medical Systems, Inc.* v. *United States*, Court No. 07-00316, dated Oct. 27, 2010, 36 pages.

International Search Report and Written Opinion dated Jan. 31, 2013 in corresponding International Application No. PCT/US2012/064018, 7 pages.

\* cited by examiner

SURGICAL LIGHT AND VIDEO CONTROL SYSTEM AND METHOD OF USE

FIELD OF THE INVENTION

The present disclosure relates generally to the field of medical treatment, and, more particularly, but not by way of limitation, to systems, methods, and apparatuses for illuminating and recording an image of an operative field during a medical procedure.

BACKGROUND

Appropriate illumination of an operative field during a medical procedure is an important tool in achieving a successful outcome. Often, there is more than one positionable light source used to illuminate the operative field. The light sources are positioned to reduce shadows within the operative field and to provide favorable line-of-sight lighting of the operative field. A healthcare provider may position the light sources to illuminate the operative field from different perspectives to provide the ideal illumination of the operative field. The light sources typically provide a favorable "birds-eye" view of the operative field. Because of the light sources favorable position, additional equipment, such as video recording devices, may be fixed to or incorporated into the light sources to capture images of the operative field. Often times the light source that is moved last provides the best view of the operative field.

In certain medical procedures, it is desirable to record the entire procedure for use as a teaching tool. Additionally, it may be desirable to record the entire procedure to provide a documented recording in a medical malpractice case or as a means to double check that all tools used during the medical procedure have been properly accounted. A visual recording may be particularly advantageous for surgical procedures in which multiple tools and sponges are used throughout the surgical procedure. While procedures are in place for accounting for the tools and sponges used during a surgery, the procedures generally involve healthcare providers noting the tools and sponges used during surgery and making sure the tools and sponges are accounted for after surgery. Using a video recording of a medical procedure may aid healthcare providers in reducing human error.

SUMMARY

According to an illustrative embodiment, a system for illuminating and capturing an image or video of an operative field during a medical procedure is presented. The system includes a first light source assembly, a second light source assembly, and a controller. The first light source assembly includes a first light source operable to illuminate the operative field from a first perspective, a first camera operable to capture the image or the video of the operative field, and a first sensor operable to detect motion from the first light source assembly. The second light source assembly includes a second light source operable to illuminate the operative field from a second perspective different from the first perspective, a second camera operable to capture the image or the video of the operative field, and a second sensor operable to detect motion from the second light source assembly. The controller is in communication with the first and second light source assemblies. The controller is configured to send an operational command to record the captured image or video from the first camera or the second camera based on feedback from the first sensor and the second sensor.

In another illustrative embodiment, a method for illuminating and recording an image or a video of an operative field during a medical procedure is presented. The method includes receiving a signal from a first sensor connected to a first light source when the first light source is being positioned relative to the operative field and receiving a signal from a second sensor connected to a second light source when the second light source is being positioned relative to the operative field. The method further includes determining when the first light source was moved relative to when the second light source was moved. Responsive to determining when the first and second light sources were moved, recording the image or the video from the latest light source to have been moved.

In yet another illustrative embodiment, a method for illuminating and capturing an image or a video of an operative field during a medical procedure is presented. The method includes receiving a signal from a first motion sensor connected to a first light source responsive to the first light source being positioned relative to the operative field. A first image recording device is fixed to the first light source. The method further includes receiving a signal from a second motion sensor connected to a second light source responsive to the second light source being positioned relative to the operative field. A second image recording device is fixed to the first light source. The method further includes determining a positioning sequence of the first and second light sources, and sending a recording command to either the first image recording device or the second image recording device based on the positioning sequence.

Other features and advantages of the illustrative embodiments will become apparent with reference to the drawings and detailed description that follow.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical, structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims. Unless otherwise indicated, as used herein, "or" does not require mutual exclusivity.

Figure 1:
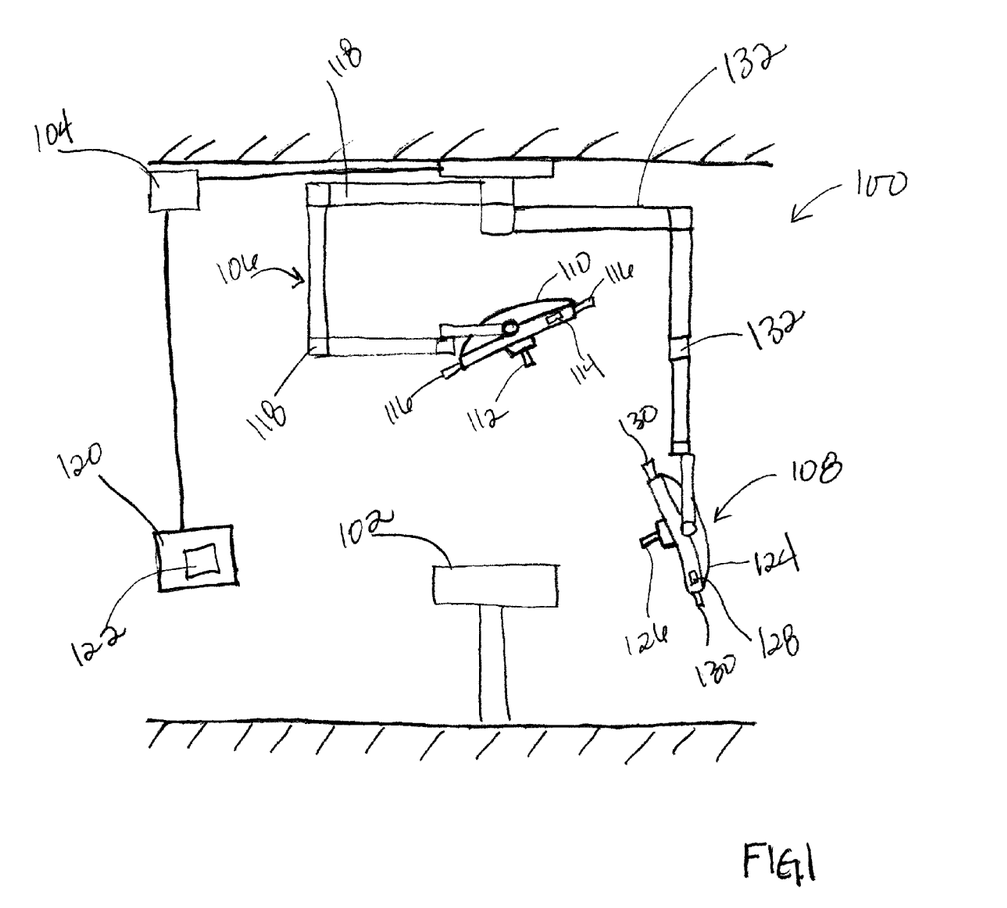
FIG. 1 is a side, perspective view, with a portion shown as a schematic diagram, of an illustrative embodiment of a system for illuminating and recording an image of an operative field during a medical procedure.

Referring now to FIG. 1, an illustrative embodiment of a system 100 for illuminating and recording an image or video of an operative field 102 during a medical procedure is presented. The image or video can be one or more still images or video, which may also include audio. For illustrative purposes, the operative field 102 is represented by a table. It should be appreciated, however, that a table is a representation of where a patient may be positioned during a medical procedure, but the operative field could include a chair or other apparatus. The operative field 102 includes and is focused on the area of the patient in which the medical procedure is being performed. While the operative field 102 may be primarily focused on the area of the patient in which the medical procedure is being performed, the operative field 102 may further include areas surrounding the patient. The system 100 includes a first light source assembly 106, a second light source assembly 108, and a controller 104 in communication with the first and second light source assemblies 106, 108. While the system 100 of FIG. 1 only illustrates the first light source assembly 106 and the second light source assembly 108, the system 100 may include additional light source assemblies. Each of the light source assemblies includes a video or image recording device.

The first light source assembly 106 is operable to illuminate the operative field 102 from a first perspective. The first light source assembly 106 includes a first light source 110, a first camera 112 and a first sensor 114. The first light source assembly 106 may also include one or more handles 116 positioned on the periphery of the first light source 110. The first light source assembly 106 may include a number of rotatable arms and joints 118 to allow the first light source 110 to be positioned relative to the operative field 102 so as to illuminate the operative field 102 from a first perspective. The number of arms and joints 118 may allow the first light source 110 to be swiveled, tilted, and rotated to offer freedom of movement. The perspective from which the first light source 110 illuminates the operative field 102 refers to the spatial orientation of the first light source 110 relative to the operative field 102, including the distance between the first light source 110 and the operative field 102, as well as the angle of the first light source 110 relative to the operative field 102. The first light source 110 is moveable so as to provide ideal illumination of the operative field 102. In one embodiment, the first light source assembly 106 moves relative to the operative field 102 independently of the second light source assembly 108.

The first light source 110 may also be referred to as a surgical lamp. The first light source 110 may be capable of providing a soft white light with high intensity, low heat, true color, shadow reduction, and without glare. The first light source 110 may include a single, double, and triple lighthead configuration. The first light source 110 is shown as being mounted to the ceiling. In one embodiment, the first light source 110 may be mounted to a side wall. In another embodiment, the first light source 110 may mounted to a floor stand. The first light source 110 is capable of providing a minimum illumination of 100,000 lux at a distance of one meter (m) between the operative field 102 and the first light source 110. The first light source 110 may illuminate the operative field 102 having a minimum diameter of 16 cm. Additionally, the focal length of the first light source 110 may be at least 65 cm. The first light source 110 may be configured to be voice and touch activated.

The first light source assembly 106 includes the first camera 112. The first camera 112 may also be referred to as an image or video recording device. The first camera 112 captures images or video of the operative field 102. The first camera 112 may be configured to capture both still images and video images. In one embodiment, the first camera 112 is a color video camera having a minimum video resolution of 720 pixels (p). The first camera 112 may stream video data live through the controller 104 to a computing device 120 having a user interface 122 or the first camera 112 may record or save the captured image or video to a storage device (not explicitly shown). The first camera 112 may be fixed to or incorporated into the first light source 110. In one embodiment, the first camera 112 is positioned in the center of the first light source 110. For example, the first light source 110 may include a triple lighthead configuration wherein each of the lightheads surround the first camera 112. In another embodiment, the first camera 112 may be positioned or fixed adjacent to the first light source 110. For example, the first camera 112 may be positioned or fixed to the handles 116. While only one camera is illustrated, it should be appreciated that more than one camera may be mounted or integrated into the first light source assembly 106.

In one embodiment, the first camera 112 may be moveable relative to the first light source 110. In another embodiment, the first camera 112 is fixed relative to the first light source 110 so that the first camera 112 moves when the first light source 110 is moved. In other words, the first camera 112 moves in tandem with the second light source 124. In this embodiment, the longitudinal axis of the first camera 112 may be substantially aligned with the optical axis of the first light source 110.

The first light source assembly 106 includes the first sensor 114. The first sensor 114 detects motion from the first light source assembly 106, and may specifically detect motion from the first light source 110. The first sensor 114 is in communication with the controller 104 and sends a signal or feedback to the controller 104 when the first light source 110 or the first light source assembly 106 is moved. The first sensor 114 may be referred to as a motion sensor and may be a gyroscope or an accelerometer. In one embodiment, the first sensor 114 is attached to the handles 116. In another embodiment, the first sensor 114 is attached to the first light source 110. The first sensor 114 may be attached to a number of places on the first light source assembly 106 so long as the first sensor 114 can detect motion from the first light source 110. While only one sensor is illustrated, it should be appreciated that more than one sensor may be mounted to the first light source assembly 106. In an alternative embodiment, the first sensor 114 can detect the touch of a human hand in addition to or instead of detecting the movement of the first light source assembly 106.

Referring still to FIG. 1, the second light source assembly 108 is operable to illuminate the operative field 102 from a second perspective different from the first perspective of the first light source assembly 106. The second light source assembly 108 includes a second light source 124, a second camera 126 and a second sensor 128. The second light source assembly 108 may also include one or more handles 130 positioned on the periphery of the second light source 124. The second light source assembly 108 may include a number of rotatable arms and joints 132 to allow the second light source 124 to be positioned relative to the operative field 102 so as to illuminate the operative field 102 from a second perspective. The number of arms and joints 132 may allow the second light source 124 to be swiveled, tilted, and rotated to offer freedom of movement. The perspective from which the second light source 124 illuminates the operative field 102 refers to the spatial orientation of the second light source 124 relative to the operative field 102, including the distance between the second light source 124 and the operative field 102, as well as the angle of the second light source 124 relative to the operative field 102. The second light source 124 is moveable so as to provide ideal illumination of the operative field 102. In one embodiment, the second light source assembly 108 moves relative to the operative field 102 independently of the first light source assembly 106.

The second light source 124 may also be referred to as a surgical lamp. The second light source 124 may be capable of providing a soft white light with high intensity, low heat, true color, shadow reduction, and without glare. The second light source 124 may include a single, double, and triple lighthead configuration. The second light source 124 is shown as being mounted to the ceiling. In one embodiment, the second light source 124 may be mounted to a side wall. In another embodiment, the second light source 124 may mounted to a floor stand. The second light source 124 is capable of providing a minimum illumination of 100,000 lux at a distance of one meter (m) between the operative field 102 and the second light source 124. The second light source 124 may illuminate the operative field 102 having a minimum diameter of 16 cm. Additionally, the focal length of the second light source 124 may be at least 65 cm. The second light source 124 may be configured to be voice and touch activated.

The second light source assembly 108 includes the second camera 126. The second camera 126 may also be referred to as an image or video recording device. The second camera 126 captures images or video of the operative field 102. The second camera 126 may be configured to capture both still images and video images. In one embodiment, the second camera 126 is a color video camera having a minimum video resolution of 720 pixels (p). The second camera 126 may stream video data live via the controller 104 to the computing device 120 having the user interface 122 or the second camera 126 may record or save the captured image or video to a storage device (not explicitly shown). The second camera 126 may be fixed to or incorporated into the second light source 124. In one embodiment, the second camera 126 is positioned in the center of the second light source 124. For example, the second light source 124 may include a triple lighthead configuration wherein each of the lightheads surround the second camera 126. In another embodiment, the second camera 126 may be positioned or fixed adjacent to the second light source 124. For example, the second camera 126 may be positioned or fixed to the handles 130. While only one camera is illustrated, it should be appreciated that more than one camera may be mounted or integrated into the second light source assembly 108.

In one embodiment, the second camera 126 may be moveable relative to the second light source 124. In another embodiment, the second camera 126 is fixed relative to the second light source 124 so that the second camera 126 moves when the second light source 124 is moved. In other words, the second camera 126 moves in tandem with the second light source 124. In this embodiment, the longitudinal axis of the second camera 126 may be substantially aligned with the optical axis of the second light source 124.

The second light source assembly 108 includes the second sensor 128. The second sensor 128 detects motion from the second light source assembly 108, and may specifically detect motion from the second light source 124. The second sensor 128 is in communication with the controller 104 and send a signal or feedback to the controller 104 when the second light source 124 or the second light source assembly 108 is moved. The second sensor 128 may be referred to as a motion sensor and may be a gyroscope or an accelerometer. In one embodiment, the second sensor 128 is attached to the handles 130. In another embodiment, the second sensor 128 is attached to the second light source 124. The second sensor 128 may be attached to a number of places on the second light source assembly 108 so long as the second sensor 128 can detect motion from the second light source 124. While only one sensor is illustrated, it should be appreciated that more than one sensor may be mounted to the second light source assembly 108. In an alternative embodiment, the second sensor 128 can detect the touch of a human hand in addition to or instead of detecting the movement of the first light source assembly 108.

Referring still to FIG. 1, the system 100 further includes the controller 104 in communication with the first and second light source assemblies 106 and 108. The controller 104 monitors and controls the functions of the first and second light source assemblies 106 and 108. The controller 104 is configured to send operational commands to the first light source 110, the second light source 124, the first camera 112, and the second camera 126 based on feedback from the first sensor 114 and the second sensor 128. As previously mentioned, the first sensor 114 and the second sensor 128 detect motion from the first light source 110 and the second light source 124, respectively. The feedback from the first sensor 114 indicates when the first light source 110 is moved and the feedback from the second sensor 128 indicates when the second light source 124 is moved.

The controller 104 may send a number of operational commands to elements of the first and second light source assemblies 106 and 108. For example, the controller 104 may send a recording command to the first or second cameras 112, 126. In one embodiment, the controller 104 sends the recording command to only one of the first camera 112 or the second camera 126. In other words, the controller 104 sends the recording command to either the first camera 112 or the second camera 126. The controller 104 may be configured to send the recording command to either the first camera 112 or the second camera 126 based on when the first light source 110 and the second light source 124 is moved. Additionally, the controller 104 may send an illumination command to the first or second light sources 110, 124 responsive to receiving feedback from the first and second sensors 114, 128 that the first or second light sources 110, 124 has moved. In other words, the first and second light sources 110, 124 may be configured to be touch activated.

It should be appreciated that while the first and second cameras 112, 126 are turned on, the first and second cameras 112, 126 capture images. However, the first and second cameras 112, 126 may not record or save the images captured until the first and second cameras 112, 126 receive a recording command from the controller 104.

The controller 104 may execute the control and monitoring functions using defined software. The controller 104 may be linked via a communications network (not shown) to a central server (not shown). The controller 104 may be complete with power supplies, a real time clock, input and output modules, memory, processors, and all other items necessary for proper and correct interfacing and operation of the controller's 104 functions.

Figure 2:
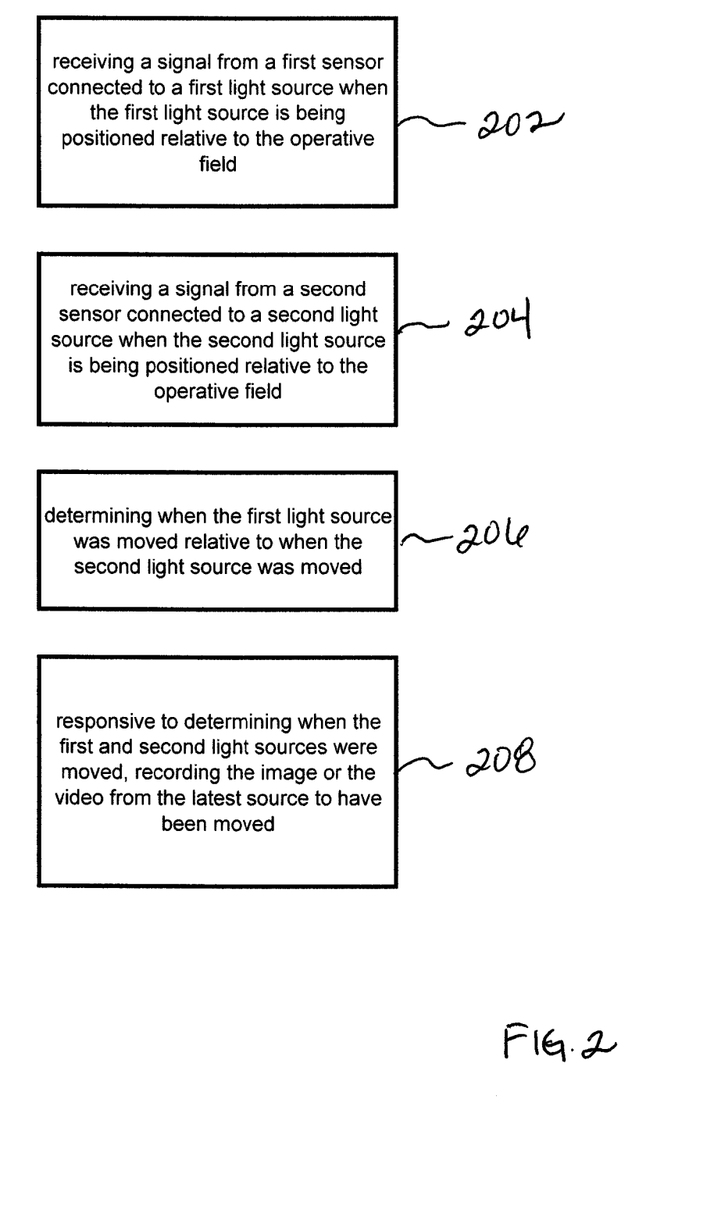
FIG. 2 is a schematic diagram of an exemplary method for operating the system illustrated in FIG. 1.

Referring now primarily to FIG. 2, but still with reference to FIG. 1, a method for illuminating and recording an image or video of the operative field 102 during a medical procedure is presented. In step 202, the controller 104 receives a signal from the first sensor 114 when the first light source 110 is being positioned relative to the operative field 102. In step 204, the controller 104 receives a signal from the second sensor 128 when the second light source 124 is being positioned relative to the operative field 102. In step 206, the controller 104 determines when the first light source 110 was moved relative to when the second light source 124 was moved. In step 208, responsive to the controller 104 determining when the first and second light sources 110, 124 were moved, the controller 104 sends a recording command to either the first camera 112 or the second camera 126 to record the image or the video from the latest light source to have been moved.

In one embodiment, the controller 104 sends the recording command to either the first camera 112 or the second camera 126 depending on which of the first or second light source 110, 124 was moved last. For example, responsive to the controller 104 determining that the first light source 110 was positioned after the second light source 124, the controller 104 sends the recording command to the first camera 112. Likewise, responsive to the controller 104 determining that the second light source 124 was positioned after the first light source 110, the controller 104 sends the recording command to the second camera 126.

Figure 3:
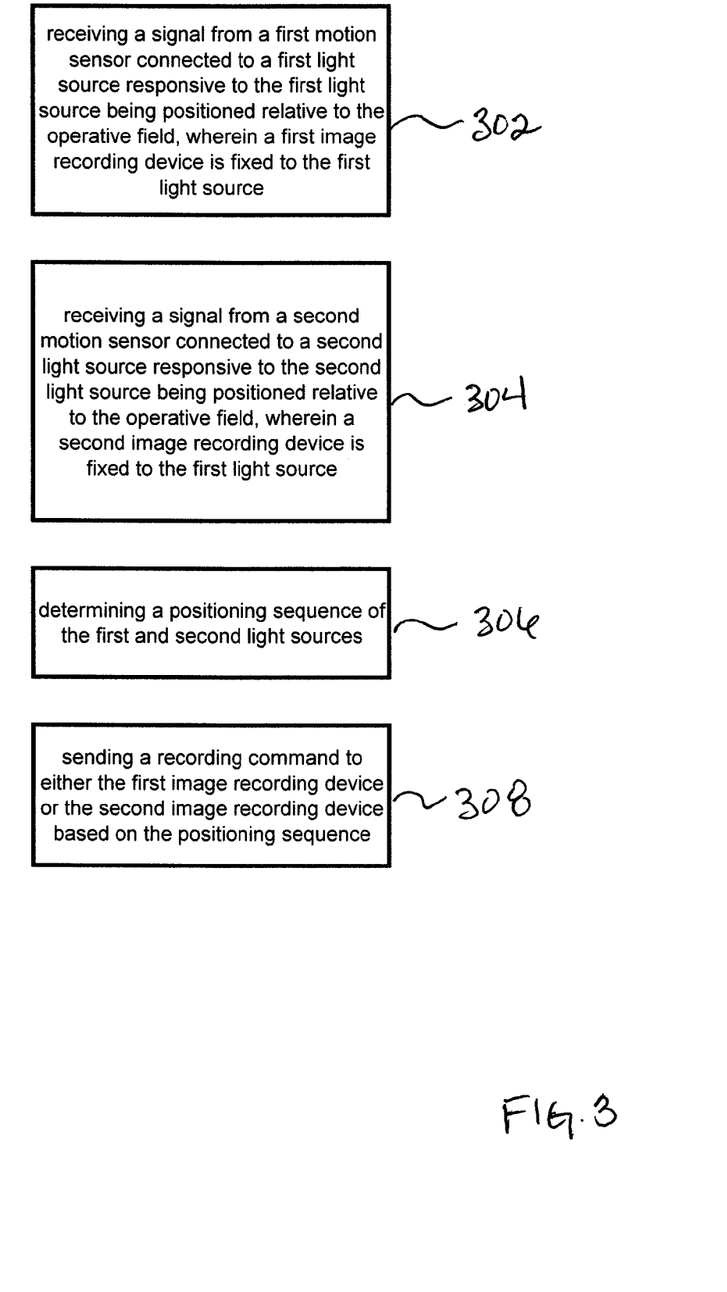
FIG. 3, is a schematic diagram of another exemplary method for operating the system illustrated in FIG. 1.

Referring now primarily to FIG. 3, but still with reference to FIG. 1, a method for illuminating and capturing an image or video of an operative field 102 during a medical procedure is presented. In step 302, the controller 104 receives a signal from the first motion sensor 114 responsive to the first light source 110 being positioned relative to the operative field 102. In step 304, the controller 104 receives a signal from the second motion sensor 128 responsive to the second light source 124 being positioned relative to the operative field 102. In step 306, the controller 104 determines a positioning sequence of the first and second light sources 110, 124. The positioning sequence indicates when the first light source 110 and the second light source 124 are moved relative to each other. The positioning sequence may indicate both the movement sequence and the time between movements. For example, the first light source 110 may be moved, 25 seconds later the first light source 110 may be moved again, and 10 seconds later, the second light source 124 may be moved. In step 308, the controller 104 sends a recording command to either the first image recording device 112 or the second image recording device based on the positioning sequence.

In one embodiment, the controller 104 sends the recording command to either the first camera 112, also referred to as the first image recording device, or the second camera 126, also referred to as the second image recording device, depending on which of the first or second light source 110, 124 was moved last in the positioning sequence. For example, responsive to the controller 104 determining that the first light source 110 was positioned after the second light source 124, the controller 104 sends the recording command to the first camera 112. Likewise, responsive to the controller 104 determining that the second light source 124 was positioned after the first light source 110, the controller 104 sends the recording command to the second camera 126. In one embodiment, there is a time delay in sending the recording command after the positioning sequence has been determined. In a specific, non-limiting embodiment, the time delay may be between 10 to 60 seconds (s). The time delay allows a healthcare provider time to adjust the lighting before recording begins. For example, if the controller 104 is configured to only send the record command to one camera based on feedback from the motion sensors, then it may be beneficial to allow the healthcare provider time to adjust the lighting before sending the recording command so the video recording does not switch back and forth between the cameras as the cameras are being adjusted.

In implementing these systems and methods to be performed by a suitably programmed computer, it is intended that the computer have a processor and a non-transitory, tangible computer readable medium, wherein the computer readable medium has program code. The program code can be made of one or more modules that carry out instructions for implementing the systems and methods herein. The processor can execute the instructions as programmed in the modules of the program code.

The systems and methods described can be implemented as a computer program product having a computer readable medium having a computer readable program code embodied therein, the computer readable program code adapted to be executed to implement a method for performing the methods described above. Each step or aspect can be performed by a different module, or a single module can perform more than a single step.

The systems and methods described herein as software can be executed on at least one server, though it is understood that they can be configured in other ways and retain its functionality. The above-described technology can be implemented on known devices such as a personal computer, a special purpose computer, cellular telephone, personal digital assistant (PDA), a programmed microprocessor or microcontroller and peripheral integrated circuit element(s), and ASIC or other integrated circuit, a digital signal processor, a hard-wired electronic or logic circuit such as a discrete element circuit, a programmable logic device such as a PLD, PLA, FPGA, PAL, or the like. In general, any device capable of implementing the processes described herein can be used to implement the systems and techniques according to this invention.

It is to be appreciated that the various components of the technology can be located at distant portions of a distributed network and/or the Internet, or within a dedicated secure, unsecured and/or encrypted system. Thus, it should be appreciated that the components of the system can be combined into one or more devices or co-located on a particular node of a distributed network, such as a telecommunications network. As will be appreciated from the description, and for reasons of computational efficiency, the components of the system can be arranged at any location within a distributed network without affecting the operation of the system. Moreover, the components could be embedded in a dedicated machine.

Furthermore, it should be appreciated that the various links connecting the elements can be wired or wireless links, or any combination thereof, or any other known or later developed element(s) that is capable of supplying and/or communicating data to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

Moreover, the disclosed methods may be readily implemented in software, e.g., as a computer program product having one or more modules each adapted for one or more functions of the software, executed on a programmed general purpose computer, cellular telephone, PDA, a special purpose computer, a microprocessor, or the like. In these instances, the systems and methods of this invention can be implemented as a program embedded on a personal computer such as a JAVA®, CGI or Perl script, as a resource residing on a server or graphics workstation, as a routine embedded in a dedicated image system, or the like. The systems and methods of this invention can also be implemented by physically incorporating this system and method into a software and/or hardware system, such as the hardware and software systems of a computer. Such computer program products and systems can be distributed and employ a client-server architecture.

The embodiments described above are intended to be exemplary. One skilled in the art recognizes that numerous alternative components and embodiments that may be substituted for the particular examples described herein and still fall within the scope of the invention.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

What is claimed is:

1. A system for illuminating and capturing an image or video of an operative field during a medical procedure, the system comprising:
    a first light source assembly comprising:
        a first light source operable to illuminate the operative field from a first perspective;
        a first camera operable to capture the image or the video of the operative field; and
        a first sensor operable to detect motion from the first light source assembly;
    a second light source assembly comprising:
        a second light source operable to illuminate the operative field from a second perspective different from the first perspective;
        a second camera operable to capture the image or the video of the operative field; and
        a second sensor operable to detect motion from the second light source assembly; and
    a controller in communication with the first and second light source assemblies, the controller configured to send an operational command to record the captured image or video from the first camera or the second camera based on feedback of a positioning sequence of the first and second light source assemblies received from the first sensor and the second sensor.

2. The system of claim 1, wherein the first sensor detects motion from the first light source and the second sensor detects motion from the second light source.

3. The system of claim 1, wherein:
    the feedback from the first sensor indicates when the first light source is moved;
    the feedback from the second sensor indicates when the second light source is moved;
    the controller is configured to send the operational command to record the captured image or video to either the first camera or the second camera based on respective times when the first light source and the second light source were moved.

4. The system of claim 1, wherein:
    responsive to the controller receiving feedback from the first sensor indicating that the first light source has been moved, the controller is configured to send an illumination signal to the first light source; and
    responsive to the controller receiving feedback from the second sensor indicating that the second light source has been moved, the controller is configured to send the illumination signal to the second light source.

5. The system of claim 1, wherein:
    the controller determines which of the first light source or the second light source is last moved; and
    the controller sends the operational command to record the captured image or video to the either the first camera or the second camera based on which of the first or second light source is last moved.

6. The system of claim 5, wherein the controller determines the first light source was moved last and the controller sends the operational command to record the captured image or video to the first camera.

7. The system of claim 1, wherein the first light source moves relative to the operative field independently from the second light source.

8. The system of claim 1, wherein the first camera moves in tandem with the first light source and the second camera moves in tandem with the second light source.

9. The system of claim 1 further comprising:
    a first handle attached to the first light source assembly; and
    a second handle attached to the second light source assembly.

10. The system of claim 1, wherein the first sensor and the second sensor is a gyroscope or an accelerometer.

11. A method for illuminating and recording an image or a video of an operative field during a medical procedure, the method comprising:
    receiving a signal from a first sensor connected to a first light source when the first light source is being positioned relative to the operative field;
    receiving a signal from a second sensor connected to a second light source when the second light source is being positioned relative to the operative field;
    determining when the first light source was moved relative to when the second light source was moved; and
    responsive to determining when the first and second light sources were moved, recording the image or the video from the latest light source to have been moved.

12. The method of claim 11, wherein responsive to determining that the first light source was positioned after the second light source, recording the image or the video from the first camera.

13. The method of claim 11, wherein responsive to determining that the second light source was positioned after the first light source, recording the image or the video from the second camera.

14. The method of claim 11 further comprising: responsive to receiving the signal from the first sensor, sending a command to the first light source to illuminate; and responsive to receiving the signal from the second sensor, sending a command to the second light source to illuminate.

15. The method of claim 11, wherein the first light source illuminates the operative field from a first perspective and the second light source illuminates the operative field from a second perspective different from the first perspective.

16. A method for illuminating and capturing an image or a video of an operative field during a medical procedure, the method comprising:
    receiving a signal from a first motion sensor connected to a first light source responsive to the first light source being positioned relative to the operative field, wherein a first image recording device is fixed to the first light source;
    receiving a signal from a second motion sensor connected to a second light source responsive to the second light source being positioned relative to the operative field, wherein a second image recording device is fixed to the first light source;
    determining a positioning sequence of the first and second light sources; and
    sending a recording command to either the first image recording device or the second image recording device based on the positioning sequence.

17. The method of claim 16, wherein the positioning sequence indicates that the first light source was moved last and the recording command is sent to the first image recording device.

18. The method of claim 16, wherein there is a predetermined time delay in sending the recording command after the positioning sequence has been determined.

19. The method of claim 16 further comprising:
    responsive to receiving the signal from the first motion sensor, sending a command to the first light source to illuminate; and
    responsive to receiving the signal from the second motion sensor, sending a command to the second light source to illuminate.

20. The method of claim 16, wherein the first light source illuminates the operative field from a first perspective and the second light source illuminates the operative field from a second perspective different from the first perspective.

* * * * *